US008864047B2

(12) United States Patent
Brathuhn et al.

(10) Patent No.: US 8,864,047 B2

(45) **Date of Patent: *Oct. 21, 2014**

(54) METHOD FOR PRODUCING A MULTILAYER COMPOUND ON A CIP-CAPABLE COATING INSTALLATION AND USE OF THE MULTILAYER COMPOUND PRODUCED BY SAID METHOD FOR TRANSDERMAL APPLICATION OR THE APPLICATION IN BODY CAVITIES

(75) Inventors: Rudi Brathuhn, Neuwied (DE); Peter Schwarz, Koenigswinter (DE); Wolfgang Schaefer, Frankfurt (DE)

(73) Assignee: LTS Lohmann Therapie-Systeme AG, Andernach (DE)

(*) Notice: Subject to any disclaimer, the term of this patent is extended or adjusted under 35 U.S.C. 154(b) by 360 days.

This patent is subject to a terminal disclaimer.

(21) Appl. No.: 13/054,153

(22) PCT Filed: Jul. 20, 2009

(86) PCT No.: PCT/EP2009/005239

§ 371 (c)(1), (2), (4) Date: Jan. 14, 2011

(87) PCT Pub. No.: WO2010/009848

PCT Pub. Date: Jan. 28, 2010

(65) Prior Publication Data

US 2011/0117177 A1 May 19, 2011

(30) Foreign Application Priority Data

Jul. 24, 2008 (DE) ........................ 10 2008 034 453

(51) Int. Cl.

| | |
|---|---|
| ***B05B 15/02*** | (2006.01) |
| ***F23D 11/34*** | (2006.01) |
| ***B65G 25/00*** | (2006.01) |
| ***B66C 17/08*** | (2006.01) |
| ***F26B 19/00*** | (2006.01) |
| ***F26B 3/00*** | (2006.01) |
| ***F26B 9/00*** | (2006.01) |
| ***A61F 13/00*** | (2006.01) |
| ***A61K 9/70*** | (2006.01) |
| ***F26B 13/00*** | (2006.01) |
| ***F26B 25/00*** | (2006.01) |

(52) U.S. Cl.

CPC ................ *F26B 13/00* (2013.01); *F26B 25/00* (2013.01)

USPC ............... 239/106; 414/159; 424/443; 34/85; 34/329; 34/357; 34/620

(58) Field of Classification Search

CPC ................................ F26B 13/00; F26B 25/00

See application file for complete search history.

(56) References Cited

U.S. PATENT DOCUMENTS

| | | | | |
|---|---|---|---|---|
| 5,849,099 | A | 12/1998 | McGuire | |
| 5,934,178 | A * | 8/1999 | Caridis et al. | 99/330 |
| 6,655,046 | B2 * | 12/2003 | Schafer et al. | 34/446 |
| 7,232,500 | B2 * | 6/2007 | Neuland et al. | 156/247 |
| 7,560,121 | B1 * | 7/2009 | Bracht et al. | 424/449 |
| 2006/0188525 | A1 * | 8/2006 | Donovan | 424/239.1 |
| 2006/0188531 | A1 * | 8/2006 | Jordan | 424/400 |
| 2006/0188554 | A1 * | 8/2006 | Nakashima et al. | 424/448 |
| 2007/0077272 | A1 * | 4/2007 | Li et al. | 424/423 |

FOREIGN PATENT DOCUMENTS

| | | | |
|---|---|---|---|
| DE | 20 2004 020631 | U1 | 9/2005 |
| DE | 20 2007 016425 | U1 | 1/2008 |
| DE | 20 2007 017655 | U1 | 3/2008 |
| EP | 0 775 882 | A1 | 5/1997 |
| WO | WO 03/061635 | A2 | 7/2003 |
| WO | WO 03061635 | A2 * | 7/2003 |
| WO | WO 2007129340 | A1 * | 11/2007 |

OTHER PUBLICATIONS

Machine Translation for EP 2063206, an equivalent for DE 20 2007 016 425, 2008.*

Machine Translation for WO 03061635, Jul. 31, 2003.*

Siro et al (Cellulose, 2010, vol. 17, pp. 459-494).*

* cited by examiner

*Primary Examiner* — Brian-Yong Kwon

*Assistant Examiner* — Mark V Stevens

(74) *Attorney, Agent, or Firm* — Ronald S. Lombard

(57) ABSTRACT

Methods for producing a mono- or multilayer composite are provided in which one or several layers are applied onto a carrier material by coating, the coated mono- or multilayer composite is dried and rolled up, and the installation is subsequently cleaned. The air circuit in the drying oven is entirely set to fresh air supply, and the drying oven is configured to be cleaned in a controlled manner. All components of the drying oven that come into contact with the product do not have to be removed during cleaning, but can be cleaned-in-place using technology integrated into the drying oven. The drying oven Outer housing is designed so that it can be lifted upwardly. All assembly parts in the drying oven interior are designed to eliminate disassembling for cleaning purposes. Transport rollers within the drying oven are designed as hollow shafts and provided with spraying nozzles.

18 Claims, 2 Drawing Sheets

METHOD FOR PRODUCING A MULTILAYER COMPOUND ON A CIP-CAPABLE COATING INSTALLATION AND USE OF THE MULTILAYER COMPOUND PRODUCED BY SAID METHOD FOR TRANSDERMAL APPLICATION OR THE APPLICATION IN BODY CAVITIES

CROSS-REFERENCE TO RELATED APPLICATIONS

This application is being filed under Rule 1.371 as a National Stage Application of pending International Application No. PCT/EP2009/005239 filed Jul. 20, 2009, which claims priority to the following parent application: German Patent Application No. 10 2008 034 453.2 filed Jul. 24, 2008. Both International Application No. PCT/EP2009/005239 and German Patent Application No. 10 2008 034 453.2 are hereby incorporated by reference herein in their entirety.

FIELD OF THE INVENTION

The present invention relates to a process for producing a multilayer composite in a cleaning-in-place capable coating installation and use of the multilayer composite produced thereby for transdermal application or application in body cavities.

BACKGROUND OF THE INVENTION

The present invention more particularly relates to a production process for a multilayer composite, in which one or more layers are firstly applied to a substrate by coating using a liquid component, the coated multilayer composite is dried thereafter and the dried multilayer composite is thereafter rolled up. The final step in the process is the cleaning of the installation, which, according to the invention, is carried out by means of a CIP system, i.e. by means of a system allowing "cleaning in place", that is integrated into the installation. The invention also relates to the use of the multilayer composite produced according to the process according to the invention as a transdermal system for the application of pharmaceutical active ingredients and the application of e.g. cosmetic active ingredients, pharmaceutical active ingredients, food supplements or medical products in body cavities.

In addition to the known forms of application for drugs such as tablets, capsules, sugar-coated tablets, drops, injections or rectal forms of application, there also is the dosage form by means of transdermal systems or wafers. Transdermal systems and wafers are produced from web-shaped materials, with the production of the web-shaped materials comprising a plurality of successive steps such as coating, drying and rolling onto rollers. By way of example, they are described in WO 03/61635. Cleaning the installation as a final work step during operation usually follows the actual procedure of production. This is because the installation should be available as quickly as possible for the production of another, new recipe in order to avoid uneconomical downtime. Furthermore, it should be possible to reliably validate the cleaning process.

During the step of coating, one or more liquid components are applied to a substrate by means of a coating installation. However, the multilayer composite, whose coating is complete after this, still contains a relatively high proportion of liquid, which is usually removed by heat in the next successive production step.

The multilayer composite with a completed coating is therefore fed into a drying oven for drying, the latter preferably being operated in continuous operation. The drying oven can comprise one or more drying zones. The individual drying zones are different in terms of their respectively differing temperatures and amounts of air. Additionally, each drying zone should possess its own air control, into which filter and heating elements are usually integrated as well. The action of the heat in the drying oven on the coated multilayer composite allows the humidity from the coated multilayer composite to escape into the airflow. In order to keep the humidity in the airflow stable, dry fresh air has to be supplied, and it is used to replace the used up, damp air. Variations in the humidity of the fresh air supply have a direct impact on the efficiency of the drying and an indirect impact on the quality of the finished product, which should not be too damp, but not too dry either.

The dried multilayer composite emerging from the drying oven is immediately rolled onto rollers.

While the multilayer composite, which has finished drying and is rolled up, is optionally put into temporary storage or transported away, the next step of operation is the complete cleaning of the installation, which should be carried out as quickly as possible, but, at the same time, should also be carried out so thoroughly that "cross contamination", i.e. transmission of traces of contents of the material produced in the preceding production cycle in the installation to the material produced in the subsequent production cycle in the installation, can be reliably excluded. This particularly thorough cleaning process is also known as according to GMP guidelines in the terminology of the art (see Wikipedia, a free encyclopedia on the Internet). Combined therewith, the particularly uneconomical downtime of the installation should be shortened to the shortest possible time.

SUMMARY OF ADVANTAGEOUS EMBODIMENTS OF THE INVENTION

It was therefore an object of the present invention to specify a simple, but at the same time guaranteed reliable, cleaning process for the drying oven in the coating installation, which can be carried out economically on a large scale. At the same time, this should allow setting the drying of the coated multilayer composite with respect to the requirements of transdermal application systems or wafers in an optimum fashion; this includes the drying oven having multiple drying zones with controllable air supply, wherein a precise and individual control of the humidity must be ensured at all times in the individual drying zones.

This object is achieved by a process of the type mentioned at the outset, the characterizing features of which should be considered those of the air circulation being set entirely to fresh air supply during the drying of the coated multilayer composite in the drying oven and of the interior of the drying oven being able to be cleaned in a controlled fashion.

DETAILED DESCRIPTION OF ADVANTAGEOUS EMBODIMENTS OF THE INVENTION

Figure 1:
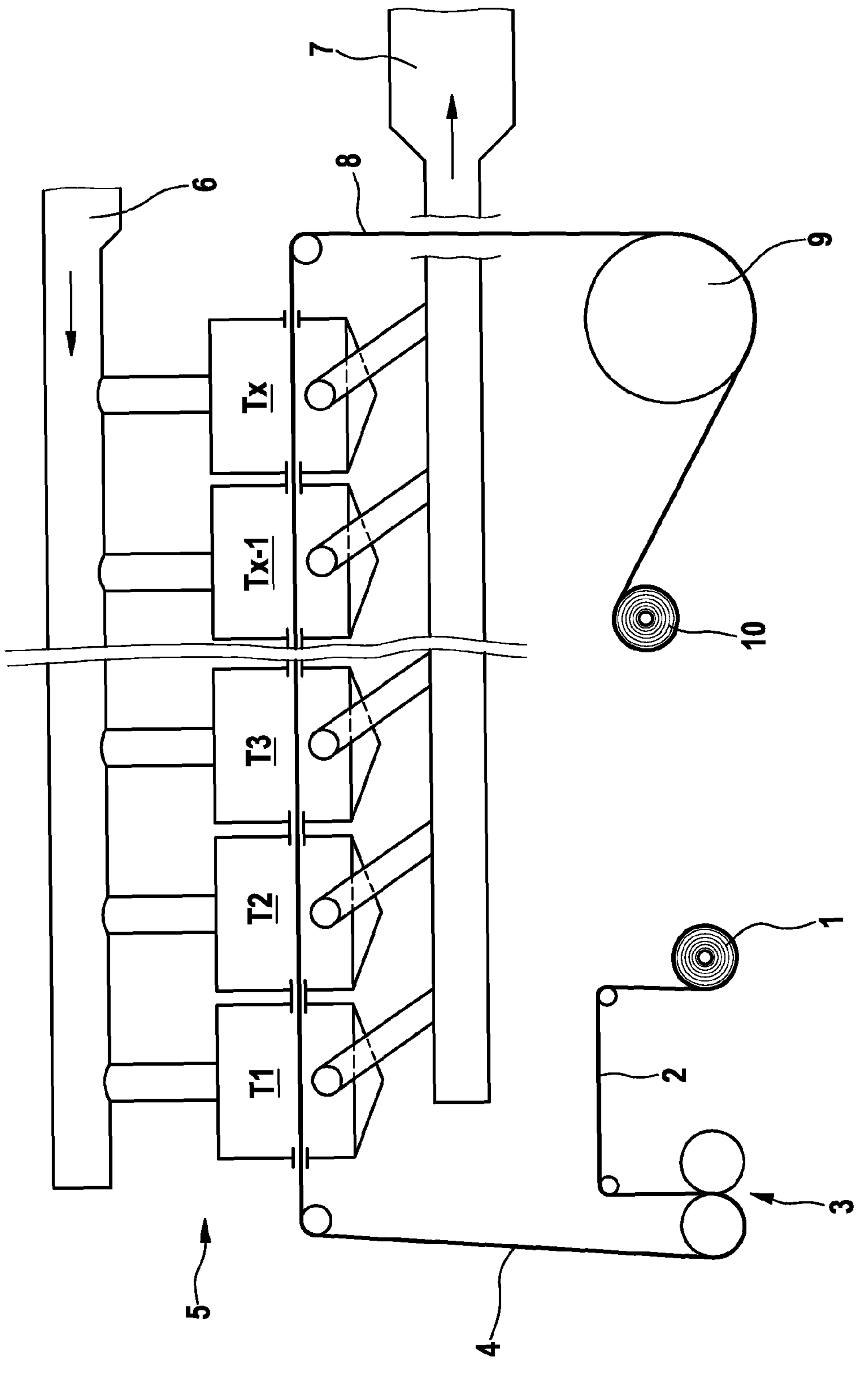
FIG. 1 schematically illustrates an exemplary method by which a multilayer composite can be produced according to the invention in a multistage process.

Web-shaped materials such as paper webs or textile webs in the form of fabrics or nonwovens from natural or artificial fibers are suitable as a substrate for the multilayer composite, but plastics films may also be utilized, which can optionally be provided with holes.

Organic raw materials in a mixture with water and/or organic solvents substantially come into question as the liquid component for coating the substrate in the process according to the invention. Mixtures of organic raw materials, which are water-soluble or can be suspended in water, are also particularly well suited. Examples of such organic raw materials are polymers such as polyvinyl alcohol, polyvinyl pyrrolidone, cellulose derivatives, polyvinyl acetate, polyethylene glycol, alginates, xanthates, gelatins and other more or less water-soluble polymers known to a person skilled in the art. If desired, the liquid components may also contain further fillers such as mannitol, lactose, calcium phosphates, glucose or sorbic-acid derivatives. Additives of active substances such as drugs, flavorings, menthol, glutamate and other additives, partly also of a volatile type, are also suitable.

According to the invention, the substrate is coated with one or more liquid components according to conventional application techniques. By way of example, the liquid components can be poured onto the substrate, applied with the aid of rollers or other relevant processes known to a person skilled in the art.

In order to clean the coating installation, all installation parts coming into contact with the substrate and/or the liquid component or components are thoroughly cleaned using a cleaning-in-place (CIP) technique. Furthermore, the remaining installation parts need to be cleaned, particularly if even the smallest amount of coating material has detached from the substrate during the coating process and/or if the contents of the coating material evaporate during the coating process and are deposited in the coating installation.

The drying oven utilized for the process according to the invention preferably comprises at least two, particularly preferably up to fourteen, drying zones in which the air circulation is completely set to fresh air supply. Here the inlet nozzles are embodied such that in each drying zone they allow uniform airing of the entire surface of the coated multilayer composite in the respective drying zone by the conditioned fresh airflow. Each individual drying zone in the drying oven has a conditioning of the supplied fresh airflow that can be controlled independently of all the other drying zones. This ensures that the optimum drying conditions can be set precisely in each drying zone via the amount of air, the air temperature and the air humidity.

The drying oven used for the process according to the invention is preferably constructed such that its entire interior can be cleaned in a controlled fashion and can be accessed easily. More particularly, this means that all components of the drying oven that may come into contact with the product produced therein do not have to be dismantled for cleaning purposes, but can be cleaned using the CIP technique with the aid of the system integrated into the drying oven. The outer housing of the drying oven is embodied such that the upper part of the drying oven can be lifted upward in order thereby to ensure simple accessibility for the upper and lower part of the drying oven. This is used to monitor the cleaning success of the CIP technique. All fixtures inside the drying oven are embodied such that cleaning does not require disassembly. Moreover, the interior of the drying oven is embodied such that it does not have dead space. This means that all corners and nooks that are susceptible to the deposition of possible contaminants are either excluded by an appropriate technical design or, if they do occur, they are screened from contaminants penetrating therein by suitable cover elements.

All transport rollers, by means of which the coated multilayer composite is moved through the drying oven and the various drying zones, are preferably embodied as hollow shafts and equipped with spray nozzles. If they are connected to a high-pressure pump, this allows very rapid cleaning of these transport rollers from the inside out and, at the same time, this also allows cleaning of their direct vicinity within the drying oven, without these parts of the drying oven needing to be dismantled. According to the invention, the spray nozzles are arranged such that all regions of the interior of the drying oven are reached by means of the CIP technique and can thus be cleaned in a controlled fashion. The transport rollers preferably rotate slowly during the cleaning process, and this optimizes the cleaning effect in the entire interior of the drying oven. The cleaning fluid required for cleaning collects in the base of the drying oven, which base has a conical design toward the bottom, and can from there either be resupplied to the high-pressure pump or simply be drained or be removed with the aid of a pump. Thus a cleaning process can be unambiguously characterized and validated.

The multilayer composite produced according to the process according to the invention is particularly suitable for use as a transdermal system for applying drugs or cosmetics or for the application in body cavities.

Figure 2:
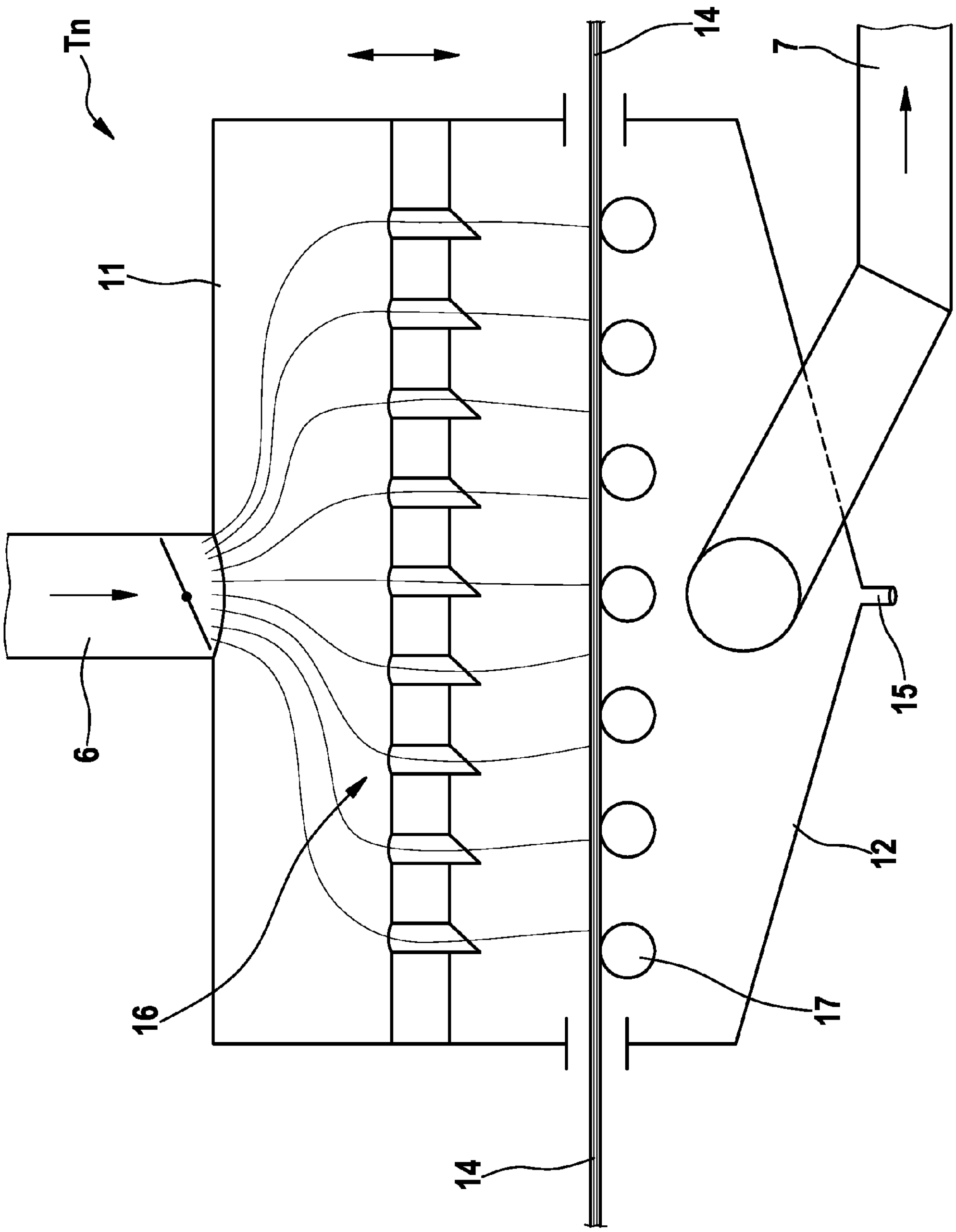
FIG. 2 schematically illustrates a vertical section through a segment of an exemplary drying oven suitable for the process according to the invention in a lateral view.

The invention shall now be explained to a person skilled in the art in an exemplary fashion and with even more clarity by means of the attached drawings as per FIG. 1 and FIG. 2.

FIG. 1 schematically shows how a multilayer composite is produced according to the invention in a multistage process.

FIG. 2 shows a schematic illustration of a vertical section through a segment of a drying oven suitable for the process according to the invention in a lateral view.

With the aid of reference signs, FIG. 1 illustrates the unwinding 1 of the substrate 2. The unwound substrate 2 is coated with one or more liquid components in the subsequent coating station 3. The coated substrate 4 is then fed to the drying oven 5, which comprises a plurality of drying zones T1, T2, T3, Tx-1 and Tx in the embodiment according to FIG. 1. The air supply 6 is illustrated on the upper part of the drying oven 5, whilst the exhaust air 7 is collected in the lower part of the drying oven 5 and discharged laterally. The dried multilayer composite 8 leaving the drying oven 5 at the drying station Tx is via a deflection roller 9 fed to a rolling up station 10 and rolled up there.

In FIG. 2, identical reference signs have the same meaning as in FIG. 1. An individual oven segment Tn of a drying oven 5 suitable for the process according to the invention is illustrated. The oven segment Tn has an upper housing part 11, which can move upward and downward in the direction of the arrow, and a lower housing part 12, which has a design that tapers in a conical fashion toward the bottom and has an outflow 15. The multilayer composite 14 to be dried in the oven segment Tn moves exactly between the upper housing part 11 and the lower housing part 12 from left to right in the direction of the arrow. The air supply 6 can be identified in the upper part of the oven segment Tn, whereas the exhaust air 7 escapes laterally toward the bottom. The air entering through the air supply 6 is applied to the multilayer composite 14 to be dried via a combined heating-nozzle system 16, with guiding rollers 17, which are equipped with spray nozzles (not illustrated), being used to move said multilayer composite through the drying segment Tn from left to right in the direction of the arrow.

The invention claimed is:

1. A process of cleaning-in-place a drying oven after producing a multilayer composite within a coating installation, comprising the following steps:

applying one or more layers to a substrate by coating with one or more liquid components, drying the coated multilayer composite in a drying oven having multiple drying segments with each of said drying segments having a separate outer housing, the drying oven air circulation is set entirely to fresh air supply during the drying of the coated multilayer composite in the drying oven, rolling up the dried multilayer composite, and cleaning-in-place the drying oven as a final step, including the interior of the outer housing and all fixtures of each of the drying segments of the drying oven having no dead spaces wherein the interior of the outer housing and all fixtures have not been cleaned and the entirety of the interior of the outer housing of each of the drying segments and all fixtures are cleaned without disassembly via a cleaning-in-place technique due to a system integrated into the drying oven, wherein the system includes each of said drying segments of said drying oven comprising transport rollers to move the coated multilayer composite through said drying segment within the drying oven, and said transport rollers are formed from hollow shafts equipped with spray nozzles for emitting cleaning fluid directed to and for contacting and cleaning without obstruction of the entirety of the interior of the outer housing of each of said drying segments and all fixtures therein without any dead spaces.

2. The process as claimed in claim 1, wherein the multilayer composite is in the form of web-shaped materials, wherein the web-shaped materials include paper webs or textile webs in the form of fabrics or nonwovens from natural or artificial fibers that are utilized as a substrate, or plastics films, which optionally include holes.

3. The process as claimed in claim 1, wherein the one or more liquid components is/are a liquid solution or liquid suspension comprising organic raw materials or mixtures thereof.

4. The process as claimed in claim 3, wherein the one or more liquid components additionally contains/contain fillers and additives of active substances.

5. The process as claimed in claim 1, wherein the substrate is coated with the one or more liquid components by pouring the one or more liquid components onto the substrate or applying the one or more liquid components with the aid of rollers.

6. The process as claimed in claim 1, wherein the outer housing of each of the drying segments of the drying oven comprises an upper part that can be lifted upward and off all fixtures in the interior of each of the drying segments of the drying oven and the interior of each of the drying segments and all fixtures therein can then be cleaned without disassembly.

7. The process as claimed in claim 1, wherein the transport rollers are further connected to a high-pressure pump which pumps the cleaning fluid through the transport rollers and into the spray nozzles integrated into the transport rollers.

8. The process as claimed in claim 7, wherein the transport rollers rotate in a controlled manner during the pumping of the cleaning fluid.

9. The process as claimed in claim 8, wherein the outer housing of each of the drying segments of the drying oven further comprises a lower housing part that tapers conically toward the bottom and the cleaning fluid flows together in the lower housing part of each of the drying segments of the drying oven and is then either drained via an outflow or returned to the high-pressure pump with the aid of a pump.

10. The process as claimed in claim 3, wherein, the organic raw materials are polyvinyl alcohol, polyvinyl pyrrolidone, cellulose, polyvinyl acetate, polyethylene glycol, alginates, xanthates, gelatins or other water-soluble polymers.

11. The process as claimed in claim 4, wherein the fillers are mannitol, lactose, calcium phosphates, glucose or sorbic acid, and the active substances are menthol, glutamate, or other active substances, and said active substances may further in part be volatile-type active substances.

12. The process as claimed in claim 1, wherein the interior of each of the drying segments of the drying oven in order to prevent dead spaces either has no corners and nooks susceptible to deposition of possible contaminants or all corners and nooks susceptible to deposition of possible contaminants are screened from contaminants penetrating therein by suitable cover elements.

13. A drying oven for a coating installation for producing a multilayer composite for transdermal application or application in body cavities, the drying oven comprising:

one or multiple drying segments with each of said drying segments—having a separate outer housing, the interior of the outer housing of each of the drying segments having no dead spaces, means for cleaning-in-place the drying oven without disassembly of the drying oven, the means for cleaning-in-place the drying oven includes each of said drying segments of said drying oven comprises transport rollers to move the coated multilayer composite through said drying segment within the drying oven, and said transport rollers are formed from hollow shafts equipped with spray nozzles for emitting cleaning fluid directed to and for contacting and cleaning without obstruction the entirety of the interior of the outer housing of each of said drying segments and all fixtures therein without any dead spaces.

14. The drying oven of claim 13, further including a high-pressure pump, the transport rollers are operatively connected to the high-pressure pump for pumping the cleaning fluid through the transport rollers and into the spray nozzles integrated into the transport rollers.

15. The drying oven of claim 14, wherein the transport rollers rotate in a controlled manner during the pumping of the cleaning fluid.

16. The drying oven of claim 15, wherein each of the drying segments of the drying oven for preventing dead spaces either has no corners and nooks susceptible to deposition of possible contaminants or all corners and nooks susceptible to deposition of possible contaminants are screened from contaminants penetrating therein by cover elements.

17. The drying oven of claim 13, wherein the outer housing of each of the drying segments of the drying oven comprises an upper part that can be lifted upward and off all fixtures inside each of the drying segments of the drying oven and the interior of each of the drying segments and all fixtures therein can then be cleaned without disassembly.

18. The drying oven of claim 13, wherein the outer housing of each of the drying segments of the drying oven further comprises a lower housing part that tapers conically toward the bottom for permitting the cleaning fluid flows together in the lower housing part of each of the drying segments of the drying oven for either draining via an outflow or for returning to the high-pressure pump with the aid of a pump. pg,20 pg,21

* * * * *